(12) United States Patent
Ono

(10) Patent No.: US 11,213,187 B2
(45) Date of Patent: Jan. 4, 2022

(54) ENDOSCOPE

(71) Applicant: FUJIFILM Corporation, Tokyo (JP)

(72) Inventor: Hirotoshi Ono, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 286 days.

(21) Appl. No.: 16/141,995

(22) Filed: Sep. 26, 2018

(65) Prior Publication Data

US 2019/0099063 A1 Apr. 4, 2019

(30) Foreign Application Priority Data

Sep. 29, 2017 (JP) .............................. JP2017-190686

(51) Int. Cl.
*A61B 1/00* (2006.01)
*A61B 1/018* (2006.01)
*A61B 1/015* (2006.01)

(52) U.S. Cl.
CPC ...... *A61B 1/00066* (2013.01); *A61B 1/00071* (2013.01); *A61B 1/015* (2013.01); *A61B 1/018* (2013.01)

(58) Field of Classification Search
CPC . A61B 1/00066; A61B 1/00071; A61B 1/018; A61B 1/015; B25C 5/0285; B25G 1/102; B43K 23/004; B60T 7/08; G05G 1/06
See application file for complete search history.

(56) References Cited

U.S. PATENT DOCUMENTS

| | | | | |
|---|---|---|---|---|
| 5,152,278 A | * | 10/1992 | Clayman | A61B 1/00066 600/131 |
| 6,508,758 B2 | | 1/2003 | Komi | |
| 6,988,295 B2 | * | 1/2006 | Tillim | A61B 17/2909 16/430 |
| 2017/0215696 A1 | | 8/2017 | Harrah et al. | |

(Continued)

FOREIGN PATENT DOCUMENTS

| | | | | |
|---|---|---|---|---|
| JP | S57109804 | | 7/1982 | |
| JP | 09173277 | * | 7/1997 | ......... A61B 1/00066 |
| JP | 09173277 A | * | 7/1997 | |

(Continued)

OTHER PUBLICATIONS

"Office Action of Japan Counterpart Application", with English translation thereof, dated Jul. 28, 2020, p. 1-p. 6.

(Continued)

*Primary Examiner* — Aaron B Fairchild
(74) *Attorney, Agent, or Firm* — JCIPRNET

(57) ABSTRACT

There is provided an endoscope from which excellent close contact feeling is obtained and which is easy to grip in a case in which an operator is to grip a grip portion.
A grip portion of an endoscope has a cross-sectional shape symmetric with respect to a second center line. The grip portion includes a first curved surface, second curved surfaces, and ridges. The first curved surface is a curved surface that is convex outward from a plane, which includes an intersection point between the second center line and the (Continued)

first curved surface and the ridge, and a plane, which includes an intersection point between the second center line and the first curved surface and the ridge. The second curved surfaces are concave inward from planes parallel to the second center line.

1 Claim, 18 Drawing Sheets

(56) References Cited

U.S. PATENT DOCUMENTS

2018/0168436 A1  6/2018  Hoshino et al.

FOREIGN PATENT DOCUMENTS

| JP | H09173277 | | 7/1997 | |
|---|---|---|---|---|
| JP | 2001212068 | | 8/2001 | |
| JP | 2001212068 A | * | 8/2001 | ........... A61B 1/0052 |
| JP | 3482288 | | 12/2003 | |
| WO | 2012083247 | | 6/2012 | |
| WO | 2013175463 | | 11/2013 | |
| WO | 2017030036 | | 2/2017 | |

OTHER PUBLICATIONS

"Search Report of Europe Counterpart Application", dated Jan. 31, 2019, p. 1-p. 5.
"Office Action of Europe Counterpart Application," dated Sep. 17, 2019, p. 1-p. 4.

* cited by examiner

ENDOSCOPE

CROSS-REFERENCE TO RELATED APPLICATION

This application claims priority under 35 USC 119 from Japanese Patent Application No. 2017-190686, filed 29 Sep. 2017, the disclosure of which is incorporated by reference herein.

BACKGROUND OF THE INVENTION

1. Field of the Invention

The present invention relates to an endoscope.

2. Description of the Related Art

In recent years, endoscopes have been widely used in a medical field and an industrial field. An endoscope used in a medical field generally includes an insertion part that is to be inserted into a subject and an operation unit that is connected to the proximal end portion of the insertion part.

In a case in which the insertion part of the endoscope is inserted into a subject to make observation and the like, an operator or the like operating the endoscope operates the endoscope while gripping the operation unit. For this reason, a grip portion, which can be gripped with one hand by an operator or the like, is provided integrally with the operation unit. Further, the operation unit is provided with various operation members, a forceps port, and the like.

An operator operates various operation members while gripping the grip portion of the operation unit. Specifically, there are many cases where the operator grips the grip portion while holding the grip portion with a palm and fingers, particularly, a middle finger, a ring finger, and a little finger, and puts a forefinger and a thumb on the operation members for easy operation at any time. As shown in FIG. 16, a grip 104 (grip portion) of an endoscope disclosed in JP1997-173277A (JP-H09-173277A) is provided with a protrusion 114 for preventing slip. Both foot portions 115 and 116 of the protrusion 114 are connected to a grip portion-outer wall 117 so as to be smoothly continuous with the grip portion-outer wall 117. The protrusion 114 is provided at a position where a finger 113 faces in a case in which an operator grips the grip 104 with one hand.

SUMMARY OF THE INVENTION

Since there are few cases where the grip portion of the operation unit of the endoscope is gripped with all five fingers as described above, the grip portion requires a shape that is easy to grip. However, since the grip portion is provided with the protrusion in the endoscope disclosed in JP1997-173277A (JP-H09-173277A), there is a case where the position of the protrusion does not correspond to the positions of the fingers of an operator in a case in which the operator grips the grip portion. That is, since there is a difference in the size of a human's hand and the length of a finger, the protrusion of the grip portion does not face the position of a finger joint and may face the ball of a finger. For this reason, close contact feeling is not good. Further, since a portion to which pressure is to be applied is concentrated in a case in which the protrusion faces the ball of a finger, there is a possibility that an unnecessary force may be applied to the finger.

An object of the invention is to provide an endoscope from which excellent close contact feeling is obtained and which is easy to grip in a case in which an operator is to grip a grip portion.

An endoscope of the invention comprises an insertion part, an operation unit, and a grip portion; a first center line and a second center line are orthogonal to each other; the grip portion includes a first curved surface that crosses the second center line, a second curved surface that is disposed at a position away from the second center line, and a ridge that is positioned between the first and second curved surfaces; the first curved surface is convex outward from a plane including an intersection point between the second center line and the first curved surface and the ridge; and the second curved surface is concave inward from a plane parallel to the second center line. The insertion part is inserted into a subject and has the first center line. The operation unit is connected to a proximal end portion of the insertion part. The grip portion is provided integrally with the operation unit and has a cross-sectional shape symmetric with respect to the second center line.

It is preferable that the first curved surface has the maximum radius of curvature at a position where the first curved surface passes through the intersection point and a radius of curvature of the first curved surface is reduced as the first curved surface is away from the second center line.

According to the endoscope of the invention, it is possible to provide an endoscope from which excellent close contact feeling is obtained and which is easy to grip in a case in which an operator is to grip a grip portion.

DESCRIPTION OF THE PREFERRED EMBODIMENTS

Schematic Structure of Endoscope

Figure 1:
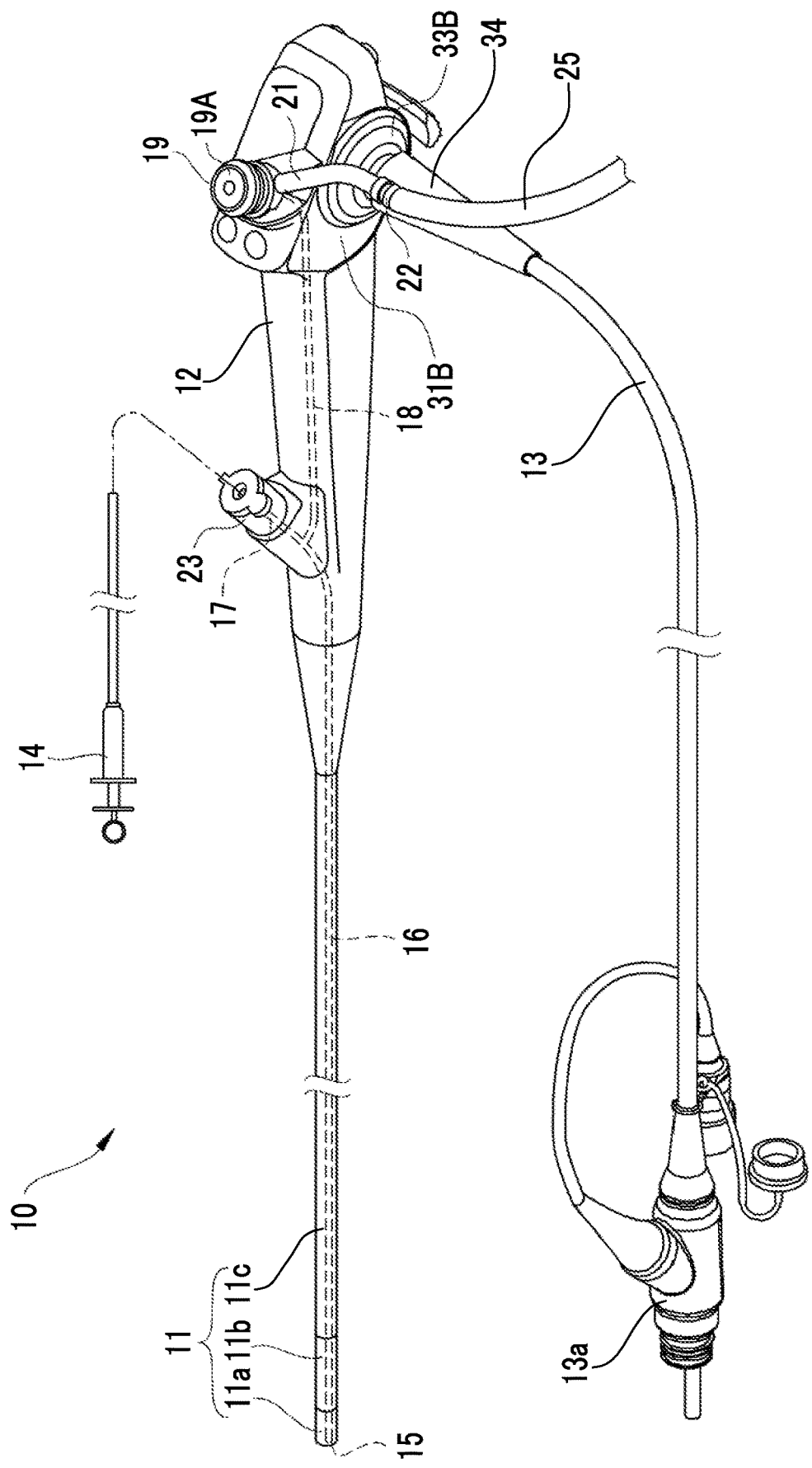
FIG. 1 is a perspective view of an endoscope.

As shown in FIG. 1, an endoscope 10 is a bronchoscope that is to be inserted into, for example, a trachea, and includes an insertion part 11 that is to be inserted into a trachea (corresponding to a subject of claims), an operation unit 12 that is connected to the proximal end portion of the insertion part 11, and a universal cord 13 that is connected to the operation unit 12. The universal cord 13 is connected to external devices, such as a processor device and a light source device (not shown), through a composite connector 13a.

The insertion part 11 includes a distal hard portion 11a, a bendable portion 11b, and a flexible tube portion 11c in this order from the distal end thereof toward the proximal end thereof. The distal end face of the distal hard portion 11a is provided with an observation window and an illumination window (not shown) in addition to a forceps outlet 15 that is an outlet for a treatment tool 14, such as forceps. An image sensor (not shown) and the like are disposed on the back of the observation window, and an optical fiber cable (not shown) is disposed on the back of the illumination window. A signal line of the image sensor and the optical fiber cable are connected to the processor device and the light source device through the insertion part 11, the operation unit 12, the universal cord 13, and the connector 13a, respectively.

A forceps channel 16 through which the treatment tool 14 is to be inserted is provided in the insertion part 11. One end of the forceps channel 16 is connected to the forceps outlet 15, and the other end thereof is connected to a forceps port 17 that is provided in the operation unit 12. Further, the forceps channel 16 is also used as a route that is used to suck in body fluid, such as blood, solids, such as dirt in the body, and the like from the forceps outlet 15. A suction channel 18 branched from the forceps channel 16 is provided in the operation unit 12, and the suction channel 18 is connected to a suction button 19 that is provided on the operation unit 12.

The suction button 19 is a disposable button that is mounted on the operation unit 12 while used, and is made of, for example, a resin. The suction button 19 includes a pipe part 21, a tube connecting port 22, and a suction valve (not shown) that is provided therein. The suction valve is connected to the suction channel 18 in the operation unit 12, and is connected to a suction pump (not shown), which is provided outside the operation unit 12, through the pipe part 21, the tube connecting port 22, and a suction tube 25.

In a case in which a pressing part 19A of the suction button 19 is operated to be pressed, a shaft part of the suction valve slides and the suction channel 18 and a pipe line of the suction pump communicate with each other. Accordingly, body fluid and the like can be sucked from the forceps outlet 15 of the insertion part 11 that is to be inserted into a subject or the like. Further, in a case in which an operation for pressing the pressing part 19A is released, the communication between the suction channel 18 and the pipe line of the suction pump is cancelled and suction from the forceps outlet 15 can be stopped.

Figure 2:
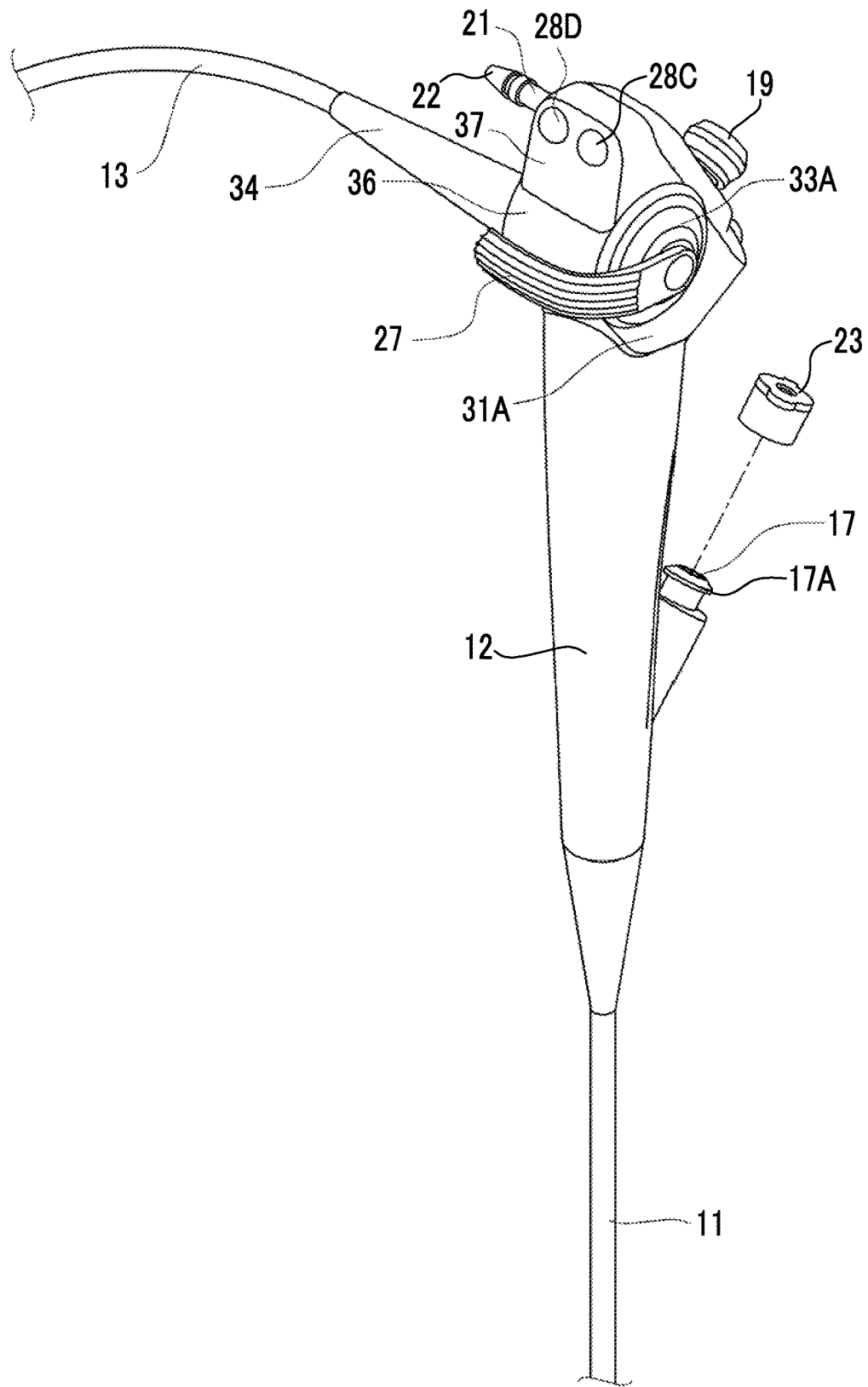
FIG. 2 is a front perspective view of an endoscope operation unit.

As shown in FIG. 2, the forceps port 17 is provided with a cap 17A and a disposable forceps valve 23 into which the treatment tool 14 can be inserted is mounted on the cap 17A.

The forceps valve 23 prevents body fluid, dirt, air, and the like, which are present in the body, from flowing back in the forceps channel 16 and from leaking to the outside from the cap 17A. The forceps valve 23 is not shown in other drawings except for FIGS. 1 and 2.

Schematic Structure of Operation Unit

Figure 3:
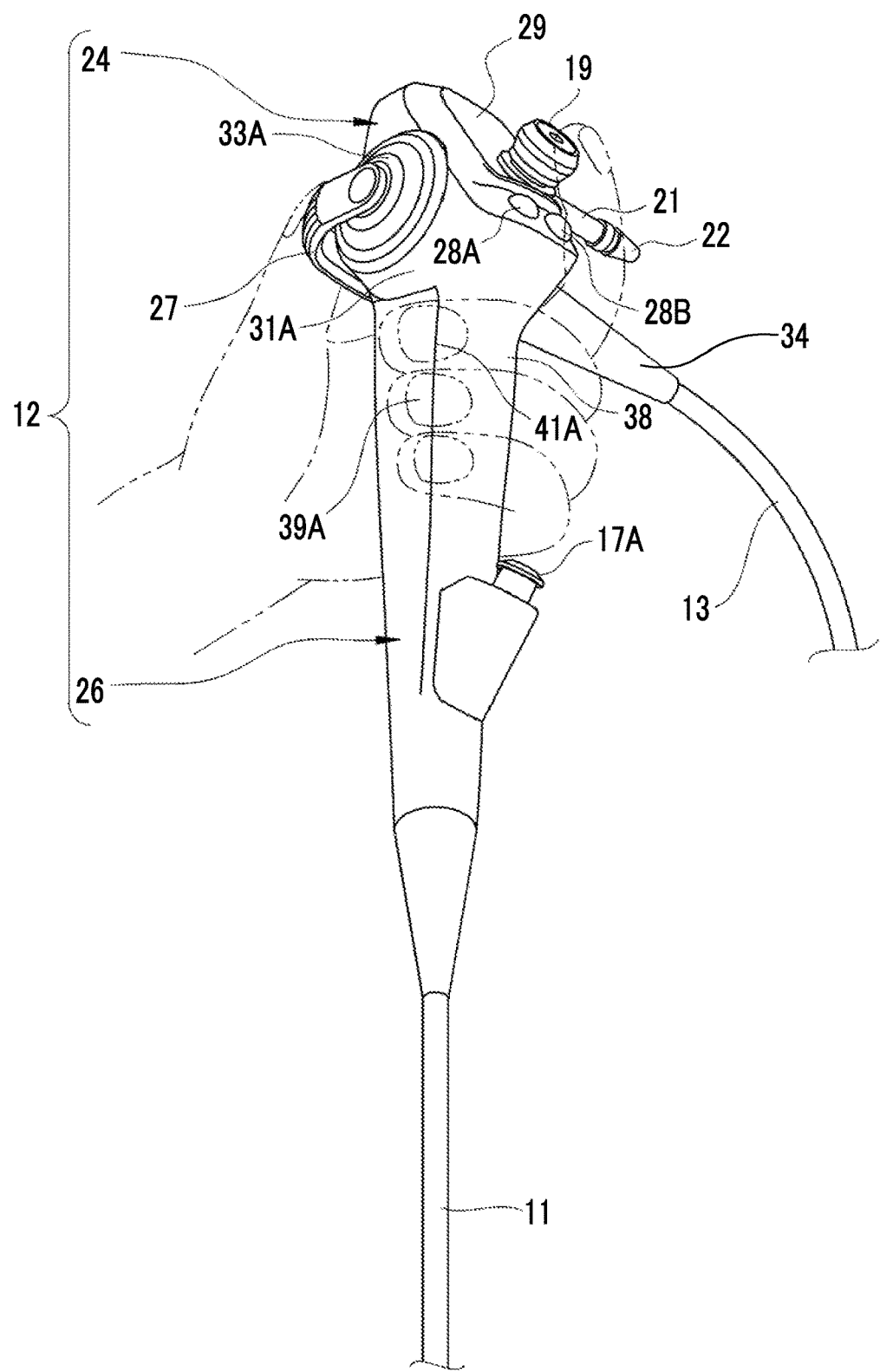
FIG. 3 is a back perspective view of the endoscope operation unit.
Figure 4:
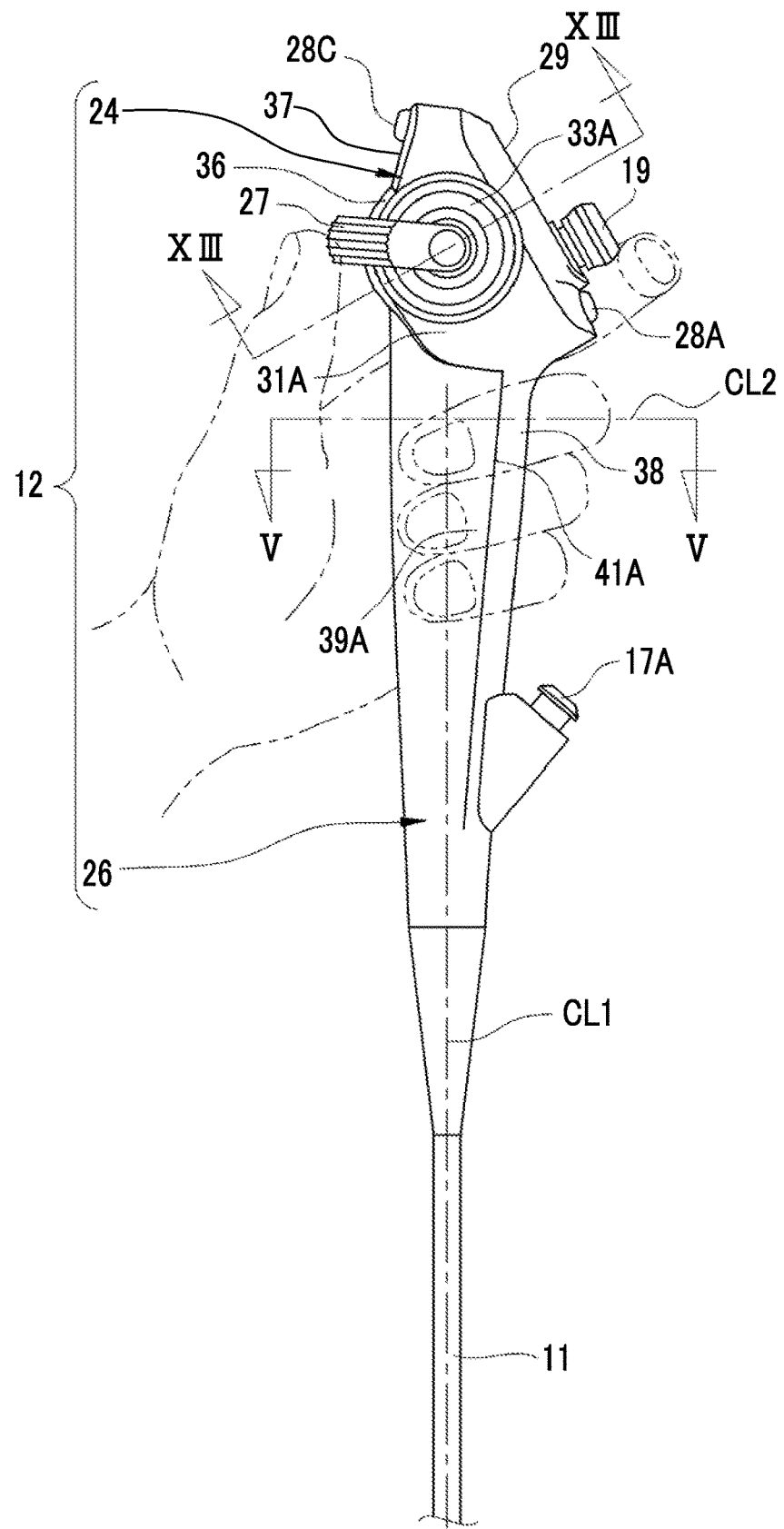
FIG. 4 is a side view of the endoscope operation unit.

As shown in FIGS. 3 and 4, the operation unit 12 includes an operation unit body 24 and a grip portion 26 that are provided integrally. Operation members, such as a bending operation lever 27, push-button switches 28A to 28D, and the suction button 19, are supported on the operation unit body 24. The bending operation lever 27 is an operation member that is used to bend the distal end portion of the insertion part 11, that is, the bendable portion 11b. For example, any of functions, such as freezing, a trigger, recording, photometric mode switching, shutter speed switching, simple special light switching, and structure emphasis, is assigned to the push-button switches 28A to 28D.

The operation unit body 24 is formed substantially in the shape of a box, and includes a front surface 29 and side surfaces 31A and 31B continuous with the front surface 29. The front surface 29 is provided with a cap portion 32 (see FIG. 7) on which the suction button 19 is mounted. Further, the push-button switches 28A and 28B are disposed on the front surface 29.

Disc parts 33A and 33B (see FIG. 1 as well) are provided at symmetrical positions on the side surfaces 31A and 31B. The disc parts 33A and 33B are components separate from the operation unit body 24 as described later, and are fixed to the side surfaces 31A and 31B. A part of the outer shapes of the side surfaces 31A and 31B are arc shapes along the outer peripheries of the disc parts 33A and 33B on the back side of the operation unit body 24. One disc part 33A is disposed between the bending operation lever 27 and the operation unit body 24. The universal cord 13 protrudes from the other disc part 33B through an opening portion (not shown), and the other disc part 33B is disposed between a sleeve 34, which covers the mount portion of the universal cord 13 and is made of rubber, and the operation unit body 24. The bending operation lever 27 is formed in an L shape so as to be bent to the back side of the operation unit body 24 from one side surface 31A.

A circumferential surface 36, which connects the disc part 33A to the disc part 33B, is formed on the back side of the operation unit body 24. An operation surface 37 on which the push-button switches 28C and 28D are disposed is provided at the upper portion of the circumferential surface 36.

The grip portion 26 has the shape of a substantially long and thin cylinder that is continuous with the insertion part 11. Further, the cap 17A is disposed on the grip portion 26 at a position near the insertion part 11.

Cross-Sectional Shape of Grip Portion

Figure 5:
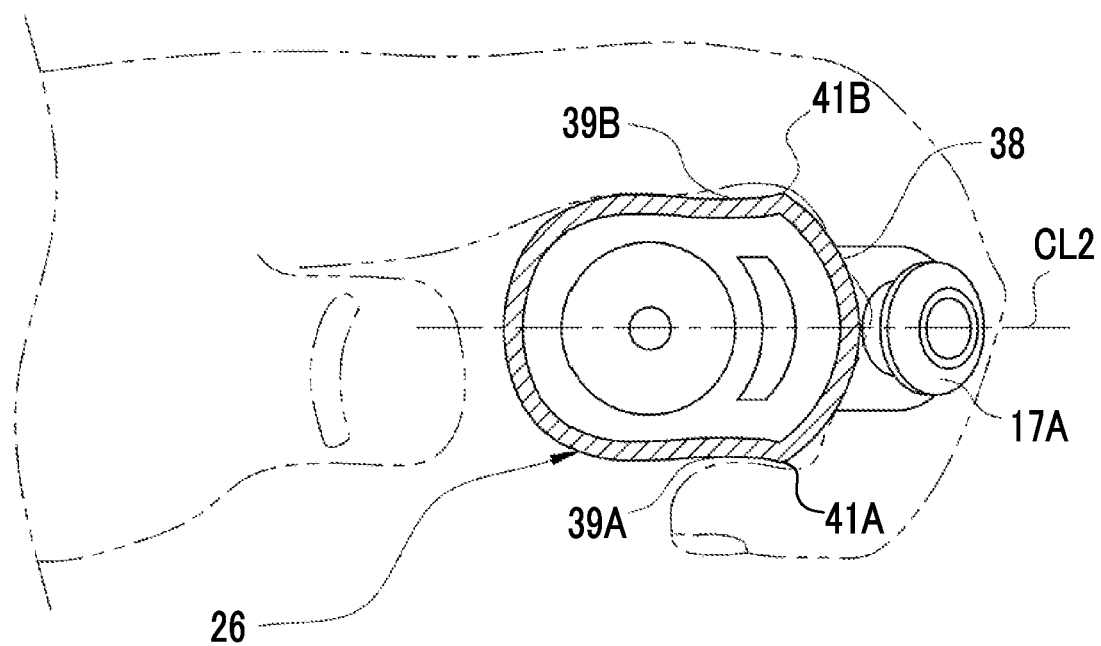
FIG. 5 is a cross-sectional view taken along line V-V of FIG. 4.

As shown in FIG. 4, the insertion part 11 has a first center line CL1. The first center line CL1 is the center line of the proximal end portion of the insertion part 11 that is connected to the operation unit 12. As shown in FIG. 5, the grip portion 26 has a cross-sectional shape that is symmetric with respect to a second center line CL2 orthogonal to the first center line CL1 (see FIG. 4) of the insertion part 11. The grip portion 26 includes a first curved surface 38, second curved surfaces 39A and 39B, and ridges 41A and 41B. The first curved surface 38 crosses the second center line CL, and the second curved surfaces 39A and 39B are disposed at positions that are away from the second center line CL2. The ridge 41A is positioned between the first curved surface 38 and the second curved surface 39A, and the ridge 41B is positioned between the first curved surface 38 and the second curved surface 39B. An internal mechanism and the like of the endoscope 10 are not shown in FIGS. 5 and 6.

Figure 6:
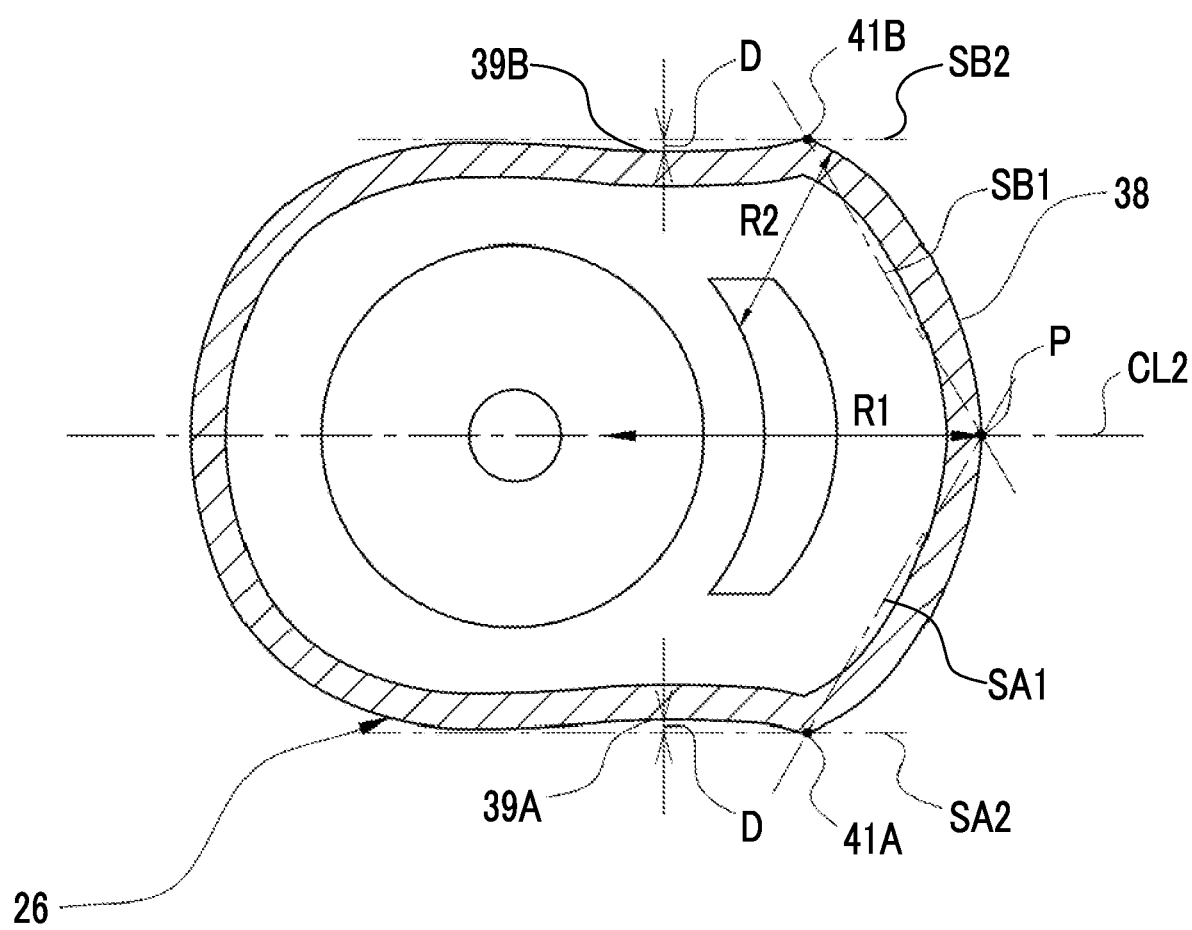
FIG. 6 is an enlarged cross-sectional view of main portions of FIG. 5.

As shown in FIG. 6, the first curved surface 38 is a curved surface that is convex outward from a plane SA1, which includes an intersection point P between the second center line CL2 and the first curved surface 38 and the ridge 41A, and a plane SB1, which includes an intersection point P between the second center line CL2 and the first curved surface 38 and the ridge 41B. The first curved surface 38 has the maximum radius R1 of curvature at the position where the first curved surface 38 passes through the intersection point P, and the radius of curvature of the first curved surface 38 is reduced as being away from the second center line CL2. That is, the first curved surface 38 has the minimum radius R2 of curvature at positions where the first curved surface 38 is most distant from the second center line CL2 (positions where the first curved surface 38 are close to the ridges 41A and 41B). Accordingly, in a case in which an operator grips the grip portion 26, particularly, in a case in which the operator grips the grip portion 26 while holding the grip portion 26 with a middle finger, a ring finger, and a little finger and a forefinger and a thumb are put on the suction button 19, the bending operation lever 27, and the like, it is easy to put the middle finger, the ring finger, and the little finger along the first curved surface 38. Further, since the grip portion 26 has a symmetrical cross-sectional shape, it is easy to grip the grip portion 26 with not only the left hand but also the right hand.

The ridges 41A and 41B are actually not lines and are formed in a round shape so that the first curved surface 38 is smoothly connected to the second curved surfaces 39A and 39B. For example, the ridges 41A and 41B are formed in a round shape having a radius in the range of, for example, 0.7 mm to 1.0 mm.

The second curved surfaces 39A and 39B are concave inward from planes SA2 and SB2 parallel to the second center line CL2. The dent amounts D of the second curved surfaces 39A and 39B from the planes SA2 and SB2 parallel to the second center line CL2 are in the range of, for example, 0.2 mm to 0.6 mm.

As described above, the grip portion 26 has a cross-sectional shape symmetric with respect to the second center line CL2, and includes the first curved surface 38 that is convex outward from the plane SA1, which includes the intersection point P and the ridge 41A, and the plane SB1, which includes the intersection point P and the ridge 41B, and the second curved surfaces 39A and 39B that are concave inward from the planes SA2 and SB2 parallel to the second center line CL2. Accordingly, the concave portion of the second curved surface 39A is caught by the ball portions of fingers in a case in which an operator grips the grip portion 26 with the right hand, and the second curved surface 39B is caught by the ball portions of fingers in a case in which an operator grips the grip portion 26 with the left hand. Therefore, it is easy for an operator to easily grip the grip portion 26. Since there is no portion to face the ball of a finger unlike in a case in which a protrusion is provided on the outer peripheral surface of a grip portion as in the related art, it is possible to grip the grip portion with excellent close contact feeling regardless of a difference in the size of a human's hand and the length of a finger. Further, since there is no portion to face the ball of a finger, an unnecessary force is not applied to a finger.

Detachable Structure of Suction Button

Figure 7:
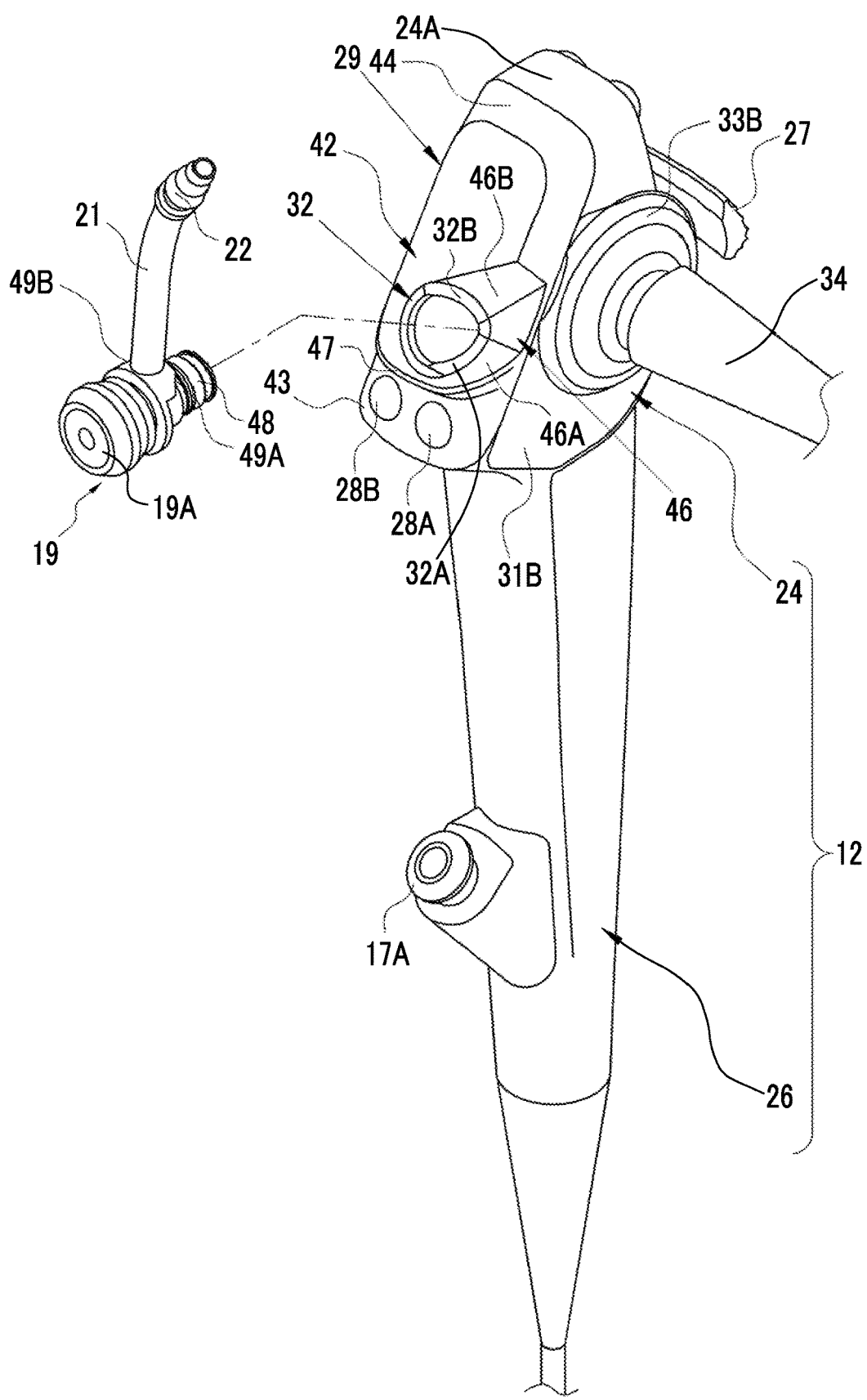
FIG. 7 is a perspective view of the endoscope operation unit from which a suction button is separated.

As shown in FIG. 7, a mounting portion 42 on which the suction button 19 is mounted and an operation surface 43 on which the push-button switches 28A and 28B are mounted are formed on the front surface 29 of the operation unit body 24. A tapered surface 44 and a notch 46 are formed on the mounting portion 42. The operation surface 43 is disposed at the lower portion of the mounting portion 42.

The tapered surface 44 is an inclined surface that is inclined toward an upper surface 24A and the side surfaces 31A and 31B from the front surface 29 of the operation unit body 24. The notch 46 is a portion where a part of the mounting portion 42 is notched toward the middle of the operation unit body 24 from a position where the tapered surface 44 is adjacent to the side surface 31B. The notch 46 includes two inclined surfaces 46A and 46B that are inclined toward the front side from the back side of the operation unit body 24.

One inclined surface 46A (guide surface) is inclined toward the operation surface 43. A projecting portion 47, which projects toward the outside of the operation unit body 24, is formed between the inclined surface 46A and the operation surface 43. The projecting portion 47 is formed in the shape of a rib that is smoothly continuous with the inclined surface 46A.

Figure 8:
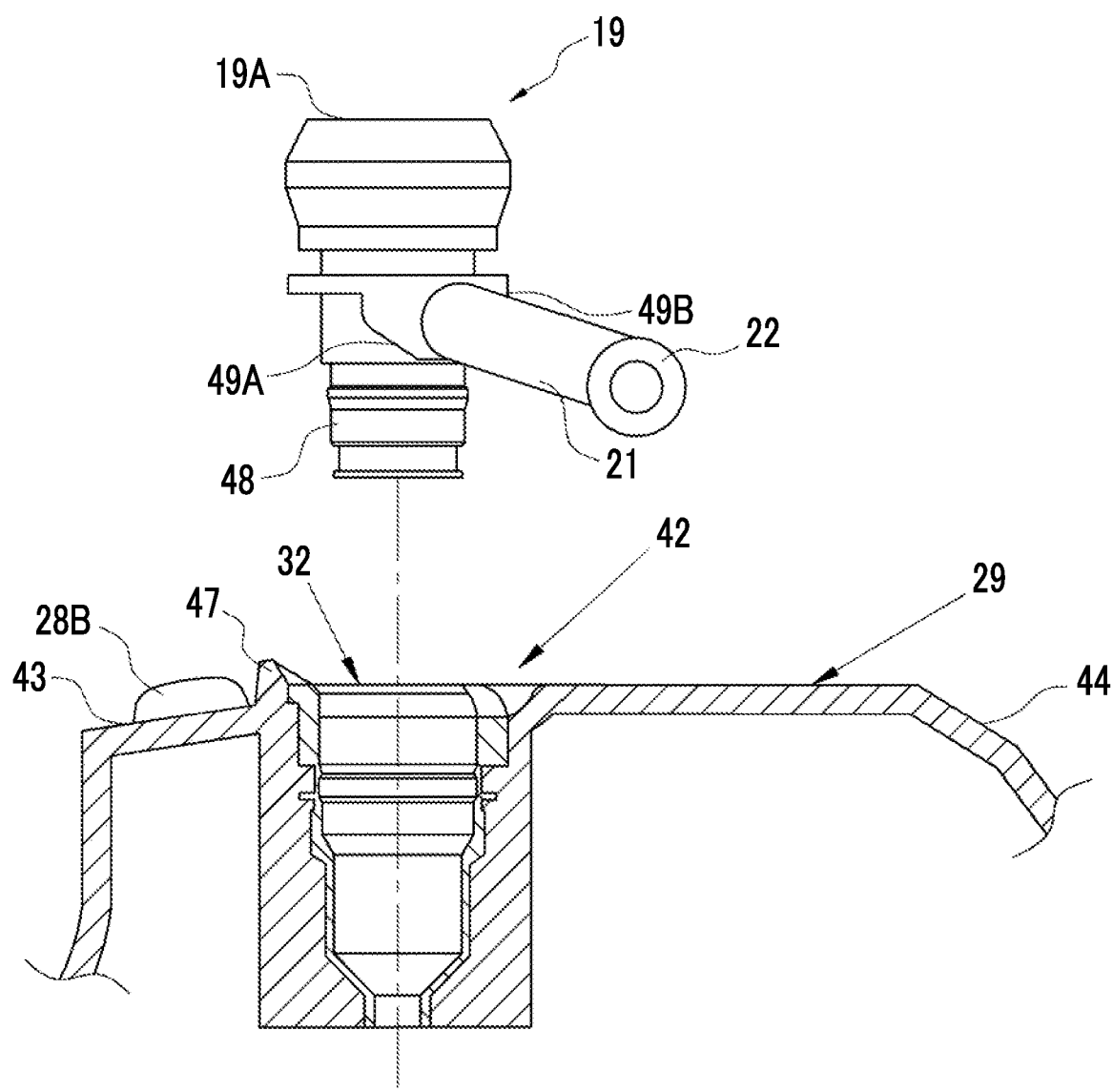
FIG. 8 is a cross-sectional view of the endoscope operation unit from which the suction button is separated.

As shown in FIG. 8, the cap portion 32 is made of, for example, metal and is fixed into the notch 46. The suction button 19 is detachably mounted on the cap portion 32. Inclined surfaces 32A and 32B are formed at portions of the cap portion 32 that are notched from the distal end face of the cap portion 32. The inclined surfaces 32A and 32B are smoothly continuous with the inclined surfaces 46A and 46B of the notch 46.

The suction button 19 includes a pressing part 19A, a fitting portion 48, the pipe part 21, and the tube connecting port 22 that are provided integrally. The suction tube 25 (see FIG. 1) is connected to the tube connecting port 22. The fitting portion 48 is connected to the suction button 19 at a position opposite to the surface of the pressing part 19A, which is to be operated to be pressed, with the pipe part 21 interposed therebetween; and is formed in a cylindrical shape. The outer peripheral surface of the fitting portion 48 is fitted to the inner peripheral surface of the cap portion 32, so that the suction button 19 is mounted on the mounting portion 42.

The pipe part 21 is disposed so as to extend in the radial direction of the pressing part 19A and the fitting portion 48. Inclined surfaces 49A and 49B (see FIGS. 9A to 9C), which are inclined toward the center of the pipe part 21 from the pressing part 19A to the fitting portion 48, are formed on both sides of the pipe part 21 at positions adjacent to the fitting portion 48. The inclined surfaces 49A and 49B are formed so as to correspond to the inclined surfaces 46A and 46B of the notch. Accordingly, in a case in which the outer peripheral surface of the fitting portion 48 is fitted to the inner peripheral surface of the cap portion 32 so that the suction button 19 is mounted on the mounting portion 42, the inclined surfaces 49A and 49B of the suction button 19 are in contact with the inclined surfaces 46A and 46B of the notch and the pipe part 21 protrudes outward from the operation unit body 24 through the notch 46.

Figure 9A:
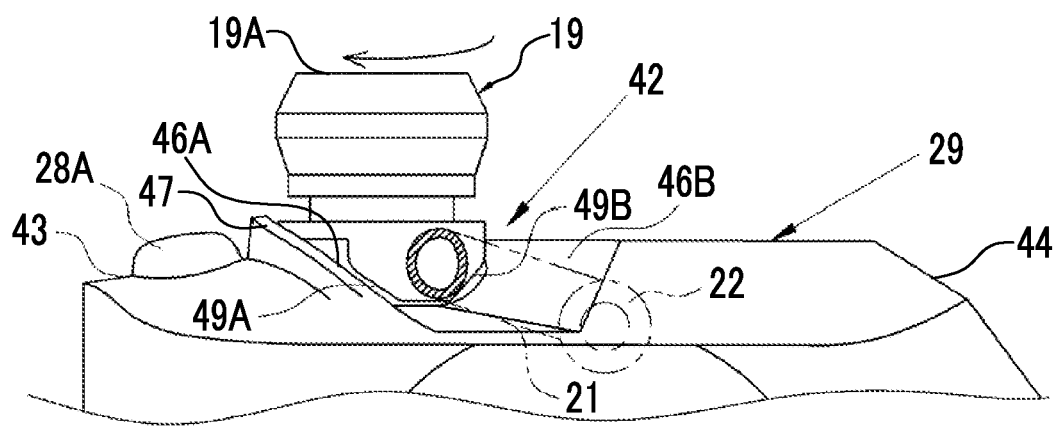
FIG. 9A is a diagram illustrating a state in which the suction button starts to be rotationally operated with respect to the endoscope operation unit for the separation of the suction button from a cap.

In a case in which the suction button 19 is to be detached, the suction button 19 is rotated about the central axis of the fitting portion 48 first as shown in FIG. 9A. In this case, the pipe part 21 is operated to be pressed so that the suction button 19 is easily rotated.

In a case in which the suction button 19 is rotated clockwise from the state shown in FIG. 9A, the inclined surface 46A of the notch 46 guides the inclined surface 49A of the suction button 19. Since the rotation of the suction button 19 is converted into movement in an axial direction by the guide of the inclined surface 49A, the suction button 19 is gradually moved in a direction where the suction button 19 is detached from the cap portion 32 as shown in FIG. 9B.

As described above, the projecting portion 47 is formed between the inclined surface 46A and the operation surface 43. In a case in which the suction button 19 is rotated, the pipe part 21 is also rotated integrally with the suction button 19 but the projecting portion 47 regulates the position of the pipe part 21. Accordingly, it is possible to prevent the pipe part 21 from being moved to the operation surface 43. For this reason, it is possible to avoid the contact between the pipe part 21 and the push-button switches 28A and 28B.

Figure 9B:
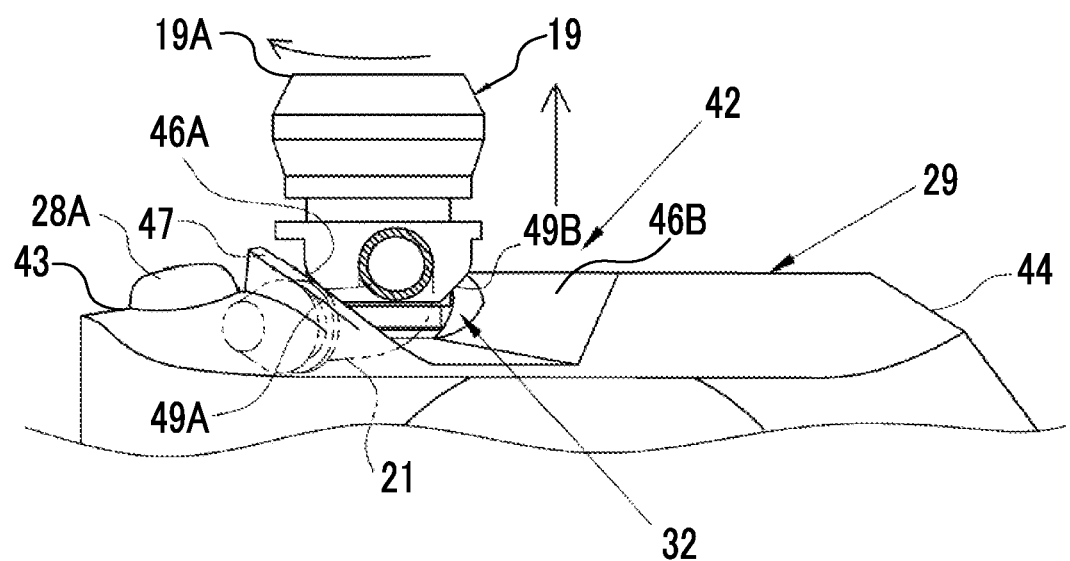
FIG. 9B is a diagram illustrating a state in which the suction button is gradually being moved along the inclined surface of the cap in the direction of an axis by a rotational operation.
Figure 9C:
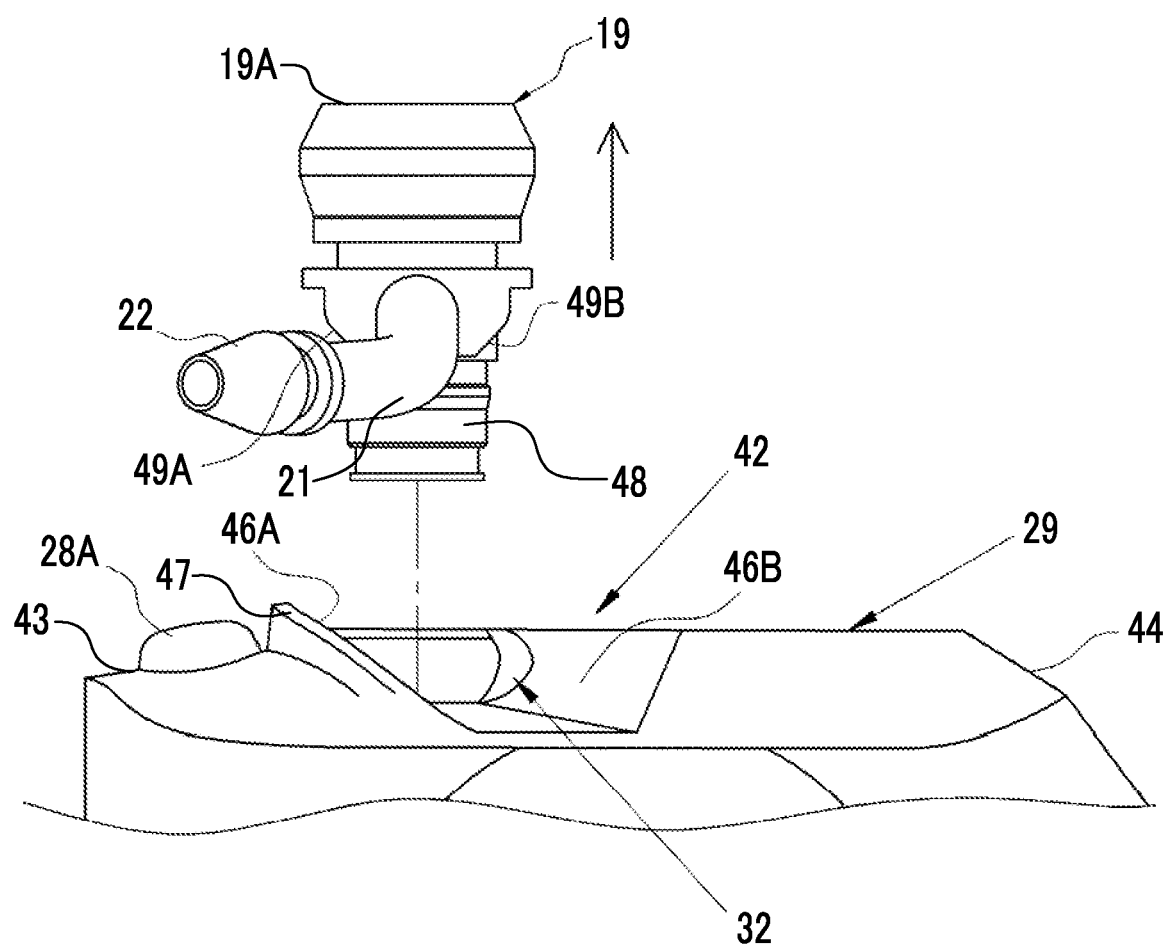
FIG. 9C is a diagram illustrating a state in which the suction button is separated.

In a case in which the suction button 19 continues to be further rotated from the state shown in FIG. 9B, the inclined surface 46A guides the inclined surface 49A, so that the suction button 19 is further moved in the axial direction. Accordingly, as shown in FIG. 9C, the fitting between the fitting portion 48 and the cap portion 32 is released and the suction button 19 is separated from the cap portion 32. In a case in which the suction button 19 is rotated counterclockwise, the inclined surface 49B of the suction button 19 is in contact with the inclined surface 46B of the notch 46 and the rotation of the suction button 19 is prevented.

Since the inclined surfaces 46A and 46B are formed on the mounting portion 42 and the inclined surfaces 49A and 49B are formed on the suction button 19 as described above, the suction button 19 can be easily detached from the mounting portion 42 by only rotation of the suction button 19. Further, since the inclined surfaces 46A and 46B are formed integrally with the operation unit body 24, high washability can be obtained.

Shape of Gasket of Lid Member

Figure 10:
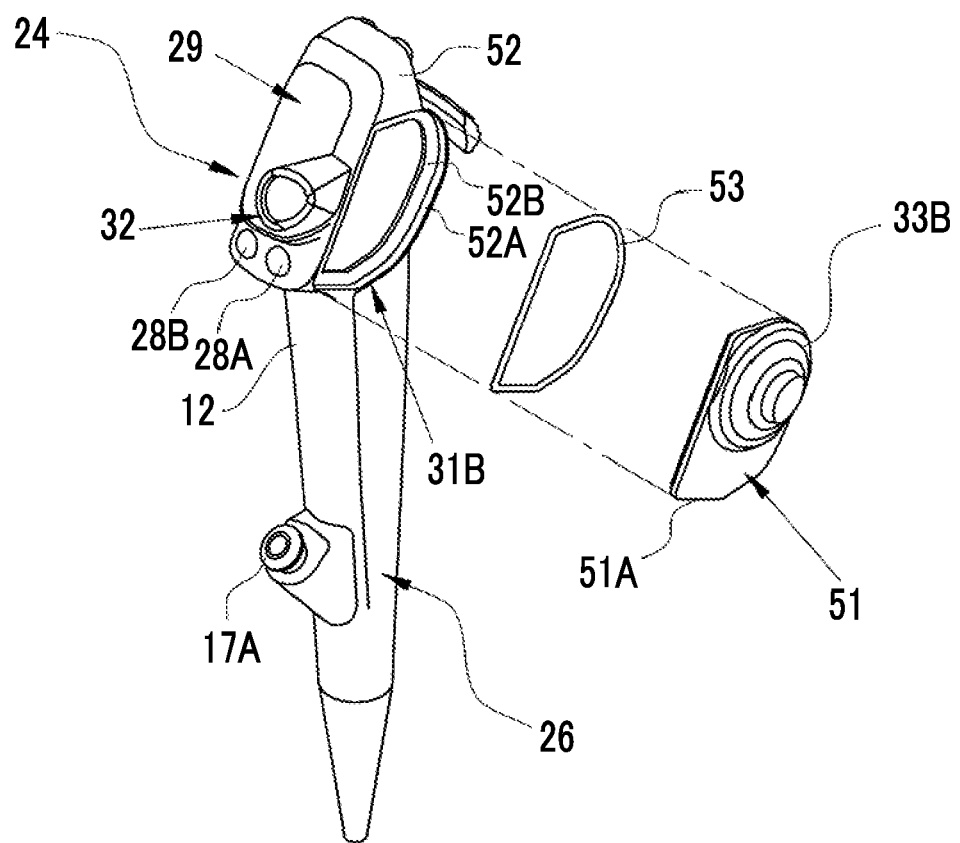
FIG. 10 is a perspective view of the endoscope operation unit from which a side lid and a gasket are separated.

As shown in FIG. 10, the operation unit body 24 includes a lid member 51 that is provided on the side surface 31B and a box-like housing 52. The disc part 33B is fixed to the lid member 51. The housing 52 houses an internal mechanism, and supports the push-button switches 28A to 28D and the like. The lid member 51 covers the inside of the housing 52 and is fixed to the housing 52 by, for example, screwing or the like. Further, there is also a case where the lid member 51 is detached from the housing 52 during the repair or maintenance of the endoscope 10. A gasket 53 formed of an elastic body is mounted between the lid member 51 and the housing 52.

Figure 11:
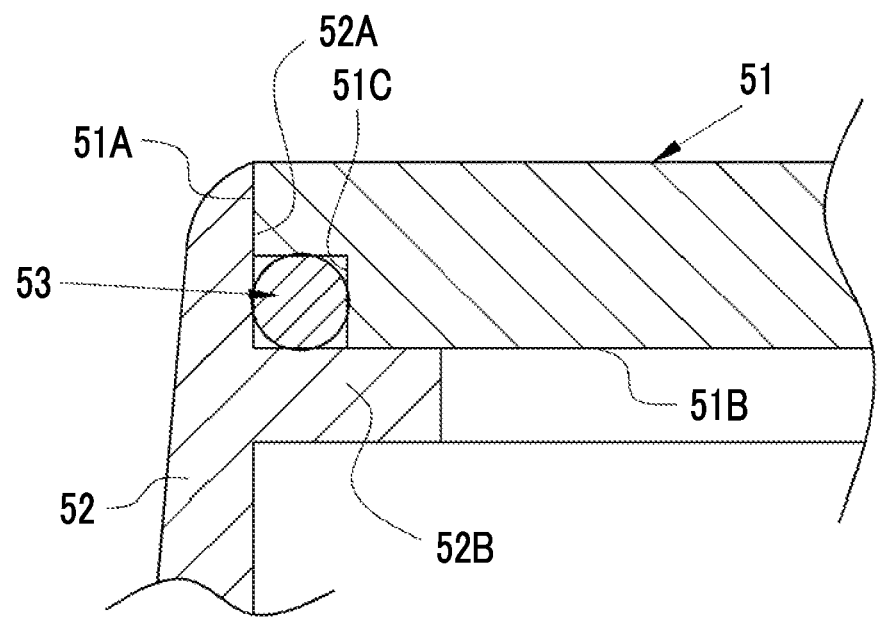
FIG. 11 is a cross-sectional view of peripheral portions of the side lid and the gasket.

As shown in FIG. 11, an opening portion 52A to which an outer peripheral surface 51A of the lid member 51 is to be fitted and a rib 52B that receives an inner wall surface 51B of the lid member 51 are formed on the housing 52. A gasket mounting portion 51C is formed on the lid member 51 along the outer peripheral surface 51A. The gasket mounting portion 51C forms a constant gap between the opening portion 52A and the rib 52B.

The gasket 53 has, for example, a circular cross-sectional shape, and has a cross-sectional area slightly larger than the cross-sectional area of the gap that is formed between the opening portion 52A and the rib 52B by the gasket mounting portion 51C. The gasket 53 is mounted on the gasket mounting portion 51C, and is mounted in a state in which the gasket 53 is interposed between the housing 52 and the lid member 51. Accordingly, the water-tightness of the operation unit body 24 can be maintained.

Figure 12:
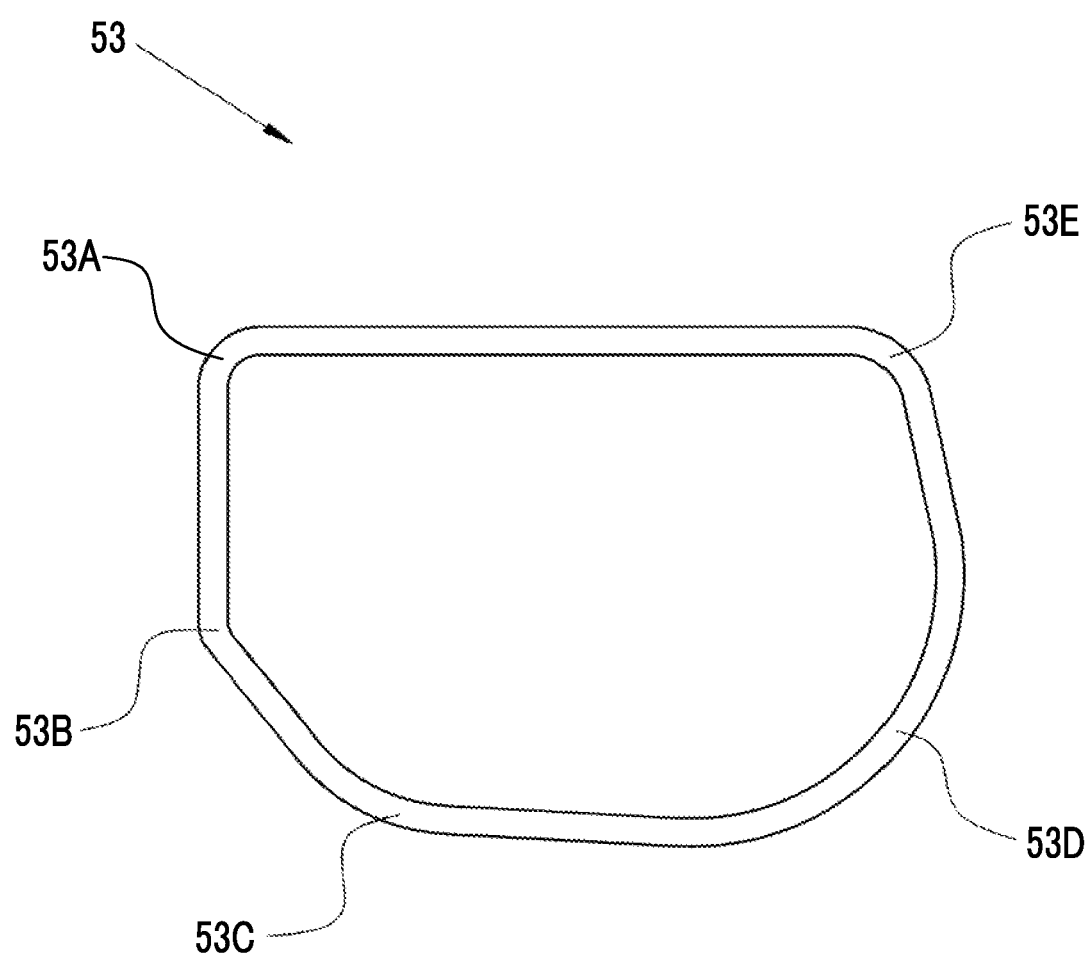
FIG. 12 is a plan view of the gasket.

As shown in FIG. 12, the gasket 53 is formed in the shape of a frame that is bent at corner portions 53A to 53E. All the corner portions 53A to 53E are bent so as to be convex outward. That is, since all the corner portions 53A to 53E are positioned on the outermost side of the gasket 53, there is no portion that is bent inward. Accordingly, the gasket 53 is adapted to be difficult to be bent inward in a case in which the gasket 53 is interposed between the housing 52 and the lid member 51. In a case in which the gasket is bent inward, a gap is likely to be formed between the housing 52 and the lid member 51. However, a gap is not formed between the housing 52 and the lid member 51 in the case of the gasket 53 of this embodiment.

Shape of Disc Part

Figure 13A:
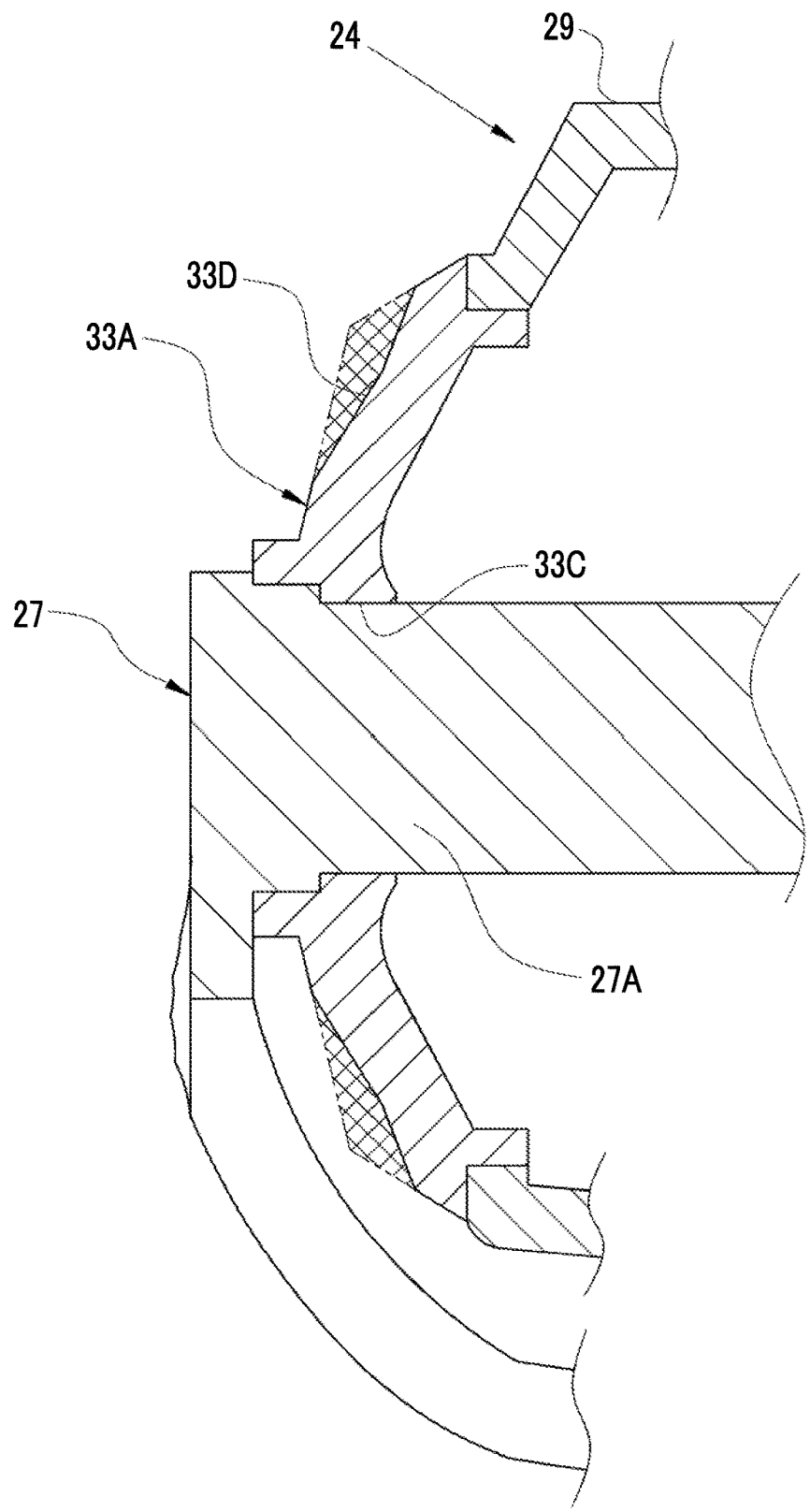
FIG. 13A is a cross-sectional view taken along line XIII-XIII of FIG. 4.

As shown in FIG. 13A, the disc part 33A is provided integrally with the side surface 31A of the operation unit body 24 and is disposed between the bending operation lever 27 and the operation unit body 24. The bending operation lever 27 is mounted on the disc part 33A through a central shaft 27A. A drive mechanism (not shown), which bends the bendable portion 11b of the insertion part 11, is connected to the central shaft 27A. In a case in which the bending operation lever 27 is rotationally operated, the drive mechanism provided in the operation unit 12 is actuated and can bend the bendable portion 11b.

The disc part 33A includes a through-hole 33C to which the central shaft 27A is to be fitted, and a tapered surface 33D of which the outer diameter is gradually reduced toward the bending operation lever 27 is formed on the disc part 33A.

To prevent the disc part 33A from being formed to be thick, the disc part 33A is formed in a cross-sectional shape where the tapered surface 33D is formed to be bent inward. A shape where the tapered surface 33D is bent inward is formed in advance in a mold that molds the housing 52 including the disc part 33A, so that the thickness of the outer portion of the tapered surface 33D is reduced (a portion shown by hatching) to prevent the disc part 33A from being formed to be thick. Accordingly, it is possible to prevent deformation (a dent referred to as a sink mark, and the like) that is caused by molding shrinkage in a case in which the disc part 33A is formed to be thick. Further, since an increase in the thickness of the disc part 33A is prevented by the bending of the tapered surface 33D without grooves or notches, washability is improved without a portion where dirt is likely to be caught (referred to as a bacteria trap). Furthermore, the disc part 33A can be allowed to have an affinity with the operation unit body 24 in terms of modeling in a range where the shape is restricted to avoid deformation caused by molding shrinkage, such as a sink mark.

Figure 13B:
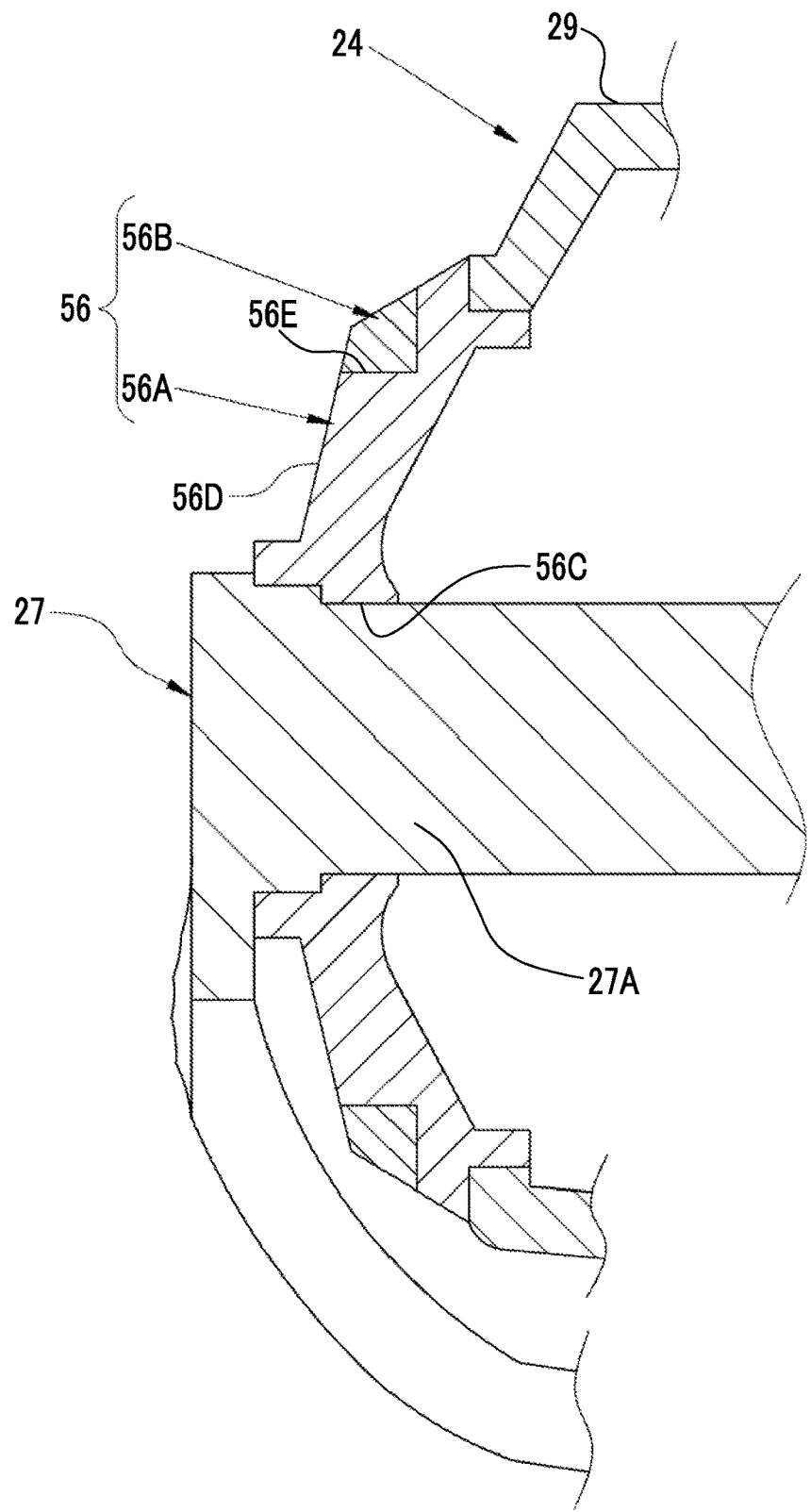
FIG. 13B is a cross-sectional view of a disc part of an endoscope in the related art.

Further, in the endoscope in the related art, a disc part 56 includes two components formed of a disc part body 56A and a ring-shaped component 56B as shown in FIG. 13B. Since a structure where the appearance of the disc part 56 is formed of a single spherical surface is considered, this structure is employed. The disc part body 56A includes a through-hole 56C, and a tapered surface 56D is formed on the disc part body 56A. A notch 56E is formed near the outer periphery of the tapered surface 56D in advance to avoid the deterioration of the waterproofness of the disc part body 56A and deformation caused by molding shrinkage. In a case in which the ring-shaped component 56B is fitted to the notch 56E, the notch 56E is hidden and the appearance of the disc part 56 is formed in the shape of a single spherical surface. Further, the ring-shaped component 56B is molded with a color different from the color of the disc part body 56A to have identifiability or characteristics.

In contrast, in the disc part 33A of this embodiment, as described above, the shape where the tapered surface 33D is bent inward is employed to reduce the thickness of the outer portion of the tapered surface 33D. Accordingly, since other components are not required, the number of components can also be reduced. In this embodiment, the disc part 33A disposed between the bending operation lever 27 and the operation unit body 24 includes the tapered surface 33D and is formed in a shape where the thickness of the outer portion of the tapered surface 33D is reduced. However, the invention is not limited thereto, and the disc part 33B disposed between the sleeve 34 and the operation unit body 24 may also include the same tapered surface 33D and may be formed in a shape where the thickness of the outer portion of the tapered surface 33D is reduced.

Shape of Bending Operation Lever

Figure 14:
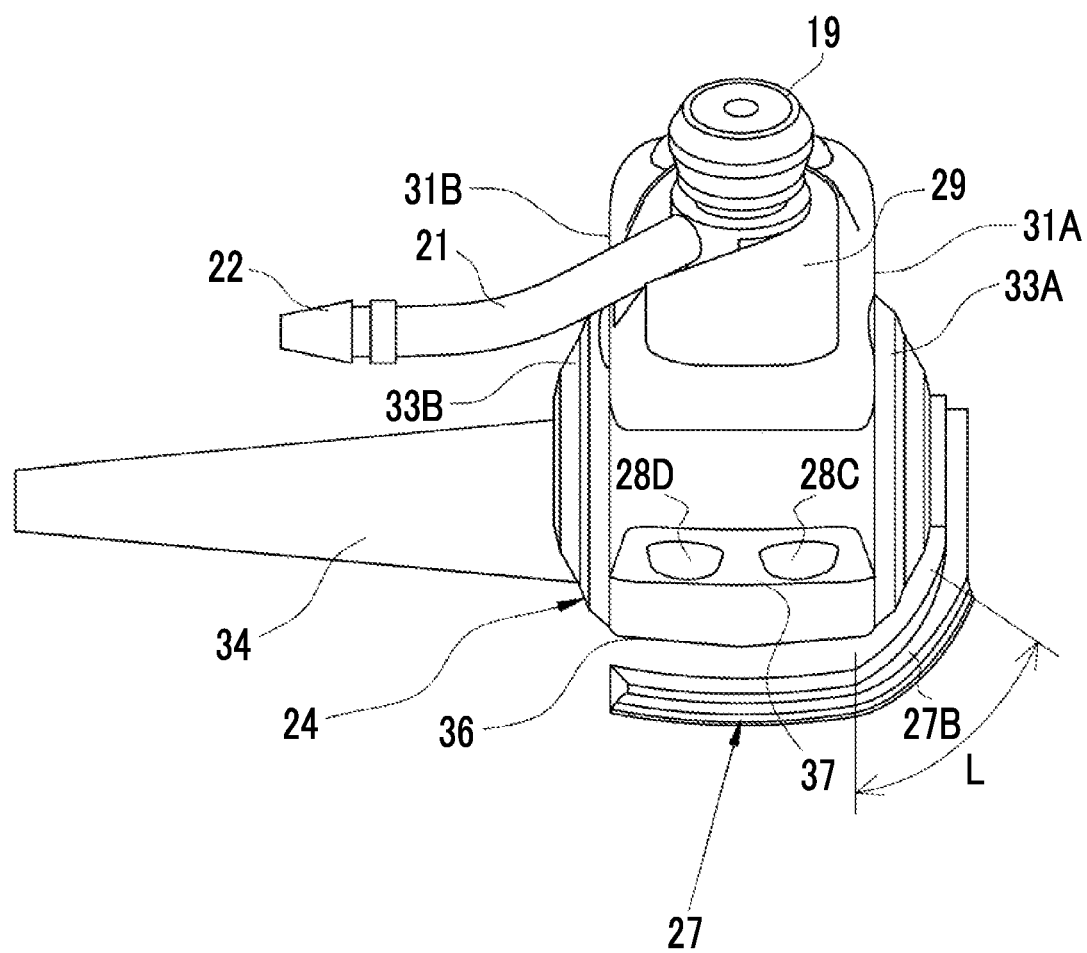
FIG. 14 is a top view of an operation unit.

As shown in FIG. 14, the bending operation lever 27 includes an arc-shaped bent portion 27B that is bent from the disc part 33A toward the circumferential surface 36 provided on the back side. Since the bent portion 27B is provided, an operator can also put the thumb on the bent portion 27B in a case in which the operator grips the grip portion 26. Accordingly, the degree of freedom in the position on which the thumb is put is high. Since the length L of the bent portion of the bending operation lever is short and the bent portion has a shape where the bent portion is bent substantially at a right angle in the endoscope in the related art that is not provided with the bent portion 27B, a finger cannot be put on the bent portion. However, a finger can be put on the bent portion in the case of the bending operation lever 27 of this embodiment.

Further, the surface of the bending operation lever 27 is formed in a knurled shape having unevenness. In the knurled shape, the distal end of a convex is edged and the dent amount of a concave portion is small. Accordingly, the gripability and washability of the bending operation lever 27 are improved.

Figure 15:
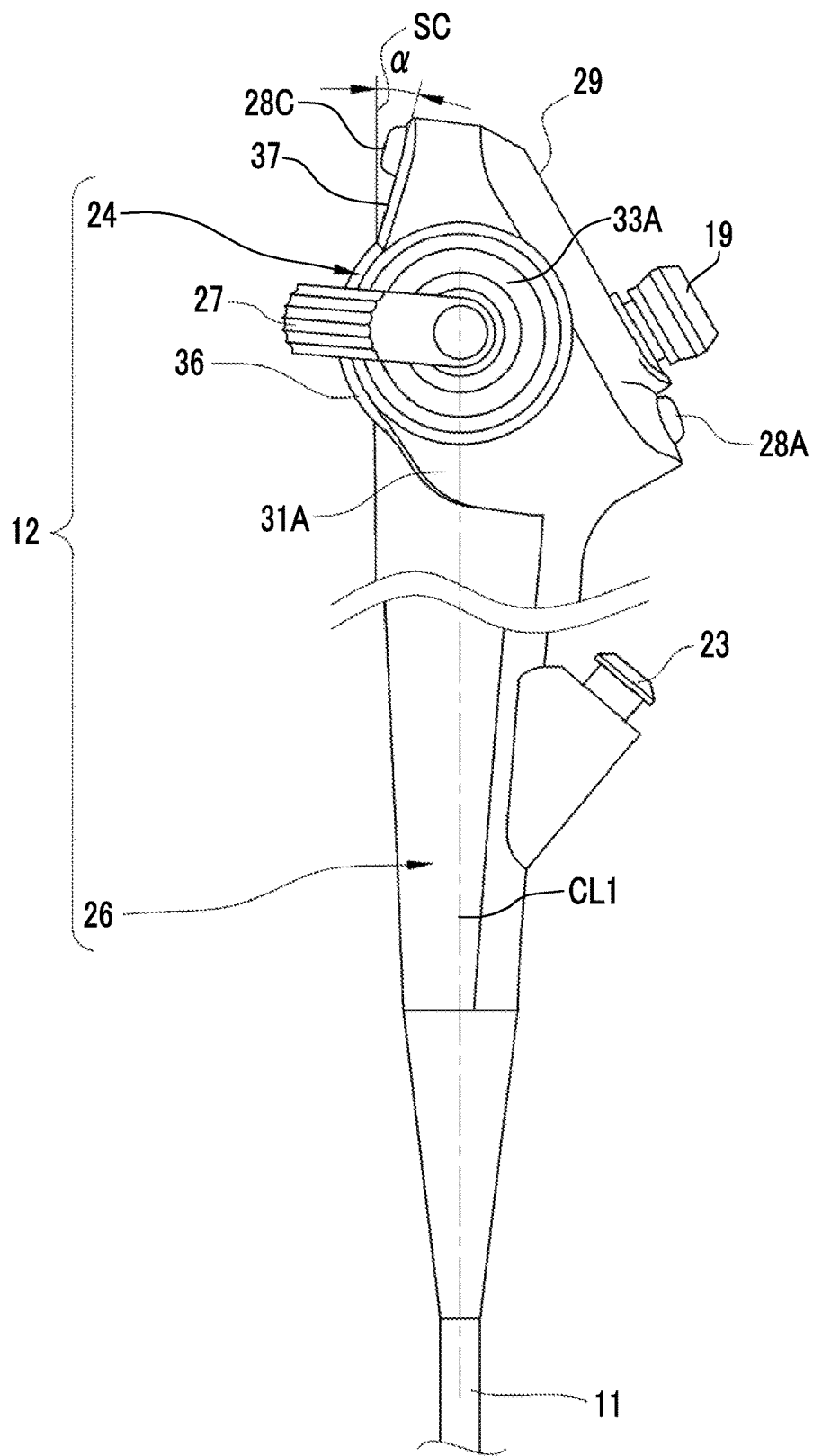
FIG. 15 is a side view of an endoscope illustrating the disposition of a back-side switch.
Figure 16:
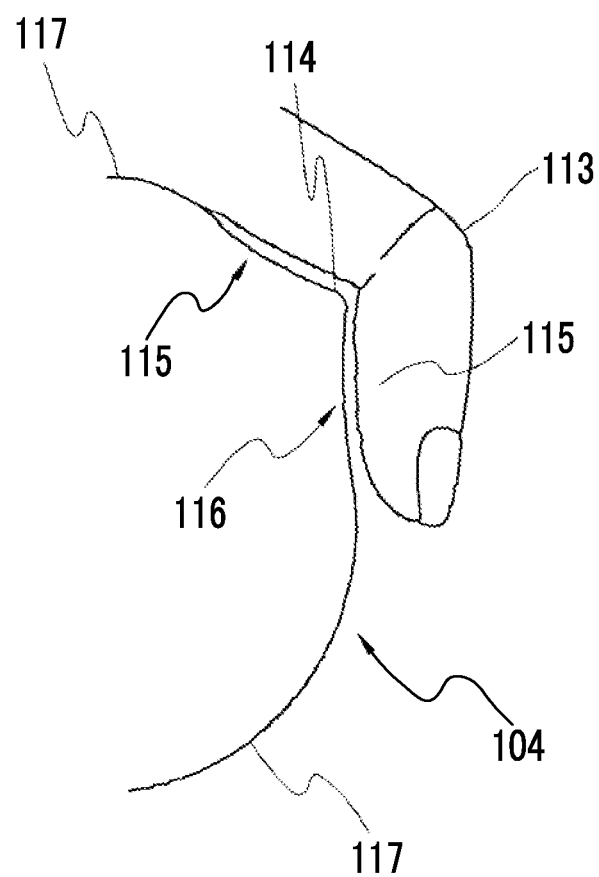
FIG. 16 is a cross-sectional view of a grip portion of the endoscope in the related art.

Inclination Angle of Operation Surface on which Push-Button Switches are Provided As shown in FIG. 15, the operation surface 37 on which the push-button switches 28C and 28D are disposed is inclined forward, that is, toward the front surface 29 from the circumferential surface 36 with respect to a plane SC parallel to the first center line CL1. It is preferable that the inclination angle α of the operation surface 37 with respect to the plane SC is in the range of about 10° to 15°. Further, the distal end faces of the push-button switches 28C and 28D are formed parallel to the operation surface 37.

Since the operation surface 37 on which the push-button switches 28C and 28D are provided is inclined forward, an operator gripping the endoscope 10 easily presses the push-button switches 28C and 28D. Furthermore, in a case in which an operator is to press the push-button switches 28C and 28D, the operator can easily press the push-button switches 28C and 28D by only moving a finger put on the bending operation lever 27, for example, a thumb forward.

The endoscope 10 to be inserted into a trachea has been described in each embodiment by way of example, but the invention can also be applied to, for example, various medical endoscopes, such as an endoscope for an ear and a nose and an endoscope for a bladder, endoscopes used for other applications, such as an industrial application, and the like.

Supplementary Note 1-1

An endoscope comprising:

an insertion part that is to be inserted into a subject;

an operation unit that is connected to a proximal end portion of the insertion part;

a mounting portion that is provided integrally with the operation unit; and a suction button that is mounted on the mounting portion, wherein a cylindrical fitting portion is connected to the suction button, the mounting portion includes a cap portion to which the fitting portion is to be fitted and a guide surface that is continuous with the cap portion, and in a case in which the suction button is rotated about the fitting portion, the rotation of the suction button is converted into movement in an axial direction by the guide of the guide surface and fitting between the fitting portion and the mounting portion is released.

Supplementary Note 1-2

The endoscope according to Supplementary Note 1-1, wherein the suction button includes a pipe part that extends in a radial direction of the fitting portion, the mounting portion includes a projecting portion that is smoothly continuous with the guide surface, and the projecting portion regulates the position of the pipe part in a case in which the suction button is rotated.

Supplementary Note 2

An endoscope comprising:

an insertion part that is to be inserted into a subject; and an operation unit that is connected to a proximal end portion of the insertion part;

wherein the operation unit includes a housing that houses an internal mechanism, a lid member that covers the inside of the housing, and a gasket that is mounted in a state in which the gasket is interposed between the housing and the lid member, and corner portions of the gasket are bent so as to be convex outward.

Supplementary Note 3-1

An endoscope comprising:

an insertion part that is to be inserted into a subject; and an operation unit that is connected to a proximal end portion of the insertion part;

wherein the operation unit includes an operation unit body, a bending operation lever that is used to bend a distal end portion of the insertion part, and a disc part that is disposed between the bending operation lever and the operation unit body, and a tapered surface having a cross-sectional shape bent inward is formed on the disc part.

Supplementary Note 3-2

An endoscope comprising:

an insertion part that is to be inserted into a subject;

an operation unit that is connected to a proximal end portion of the insertion part; and a mount portion that supports a universal cord, wherein the operation unit includes an operation unit body, a sleeve that covers the mount portion, and a disc part that is disposed between the sleeve and the operation unit body, and a tapered surface having a cross-sectional shape bent inward is formed on the disc part.

Supplementary Note 4

An endoscope comprising:

an insertion part that is to be inserted into a subject; and an operation unit that is connected to a proximal end portion of the insertion part;

wherein the operation unit includes an operation surface on which an operation member is disposed, and the operation surface is inclined with respect to a plane parallel to a center line of the insertion part.

EXPLANATION OF REFERENCES

10: endoscope
11: insertion part
11a: distal hard portion
11b: bendable portion
11c: flexible tube portion
12: operation unit
13: universal cord
13a: connector
14: treatment tool
15: forceps outlet
16: forceps channel
17: forceps port
17A: cap
18: suction channel
19: suction button
19A: pressing part
21: pipe part
22: tube connecting port
23: forceps valve
24: operation unit body
24A: upper surface
26: grip portion
27: bending operation lever
27A: central shaft
27B: bent portion
28A, 28B, 28C, 28D: button switch
29: front surface
31A, 31B: side surface
32: cap portion
32A, 32B: inclined surface
33A, 33B: disc part
33C: through-hole
33D: tapered surface
34: sleeve
36: circumferential surface
37: operation surface
38: first curved surface
39A, 39B: second curved surface
41A, 41B: ridge
42: mounting portion
43: operation surface
44: tapered surface
46A, 46B: inclined surface
47: projecting portion
48: fitting portion
49A, 49B: inclined surface
51: lid member
51A: outer peripheral surface
51B: inner wall surface
51C: gasket mounting portion
52: housing
52A: opening portion
52B: rib
53: gasket
53A, 53B, 53C, 53D, 53E: corner portion
56: disc part
56A: disc part body
56B: ring-shaped component
56C: through-hole
56D: tapered surface
56E: notch
104: grip
113: finger
114: protrusion
115: foot portion
116: foot portion
117: grip portion-outer wall
CL1: first center line
CL2: second center line
D: dent amount
L: length
P: intersection point
SA1, SB1, SA2, SB2, SC: plane
R1, R2: radius of curvature

What is claimed is:

1. An endoscope comprising:
an insertion part that is to be inserted into a subject and has a first center line;
an operation unit that is connected to a proximal end portion of the insertion part; and
a grip portion that is provided integrally with the operation unit and has a cross-sectional shape symmetric with respect to a second center line,
wherein the first center line and the second center line are orthogonal to each other,
the grip portion includes a first curved surface that crosses the second center line, a second curved surface that is disposed at a position away from the second center line, and a ridge that is positioned between the first and second curved surfaces,
the entire first curved surface is convex outward from a plane including an intersection point between the second center line and the first curved surface and the ridge, and
the second curved surface is concave inward from a plane parallel to the second center line,
wherein a radius of curvature of the first curved surface is maximum at a position where the first curved surface passes through the intersection point, and the radius of curvature of the first curved surface is decreased as the first curved surface is away from the second center line,
wherein the ridge is formed in a round shape having a radius in a range of 0.7 mm to 1.0 mm.

* * * * *